United States Patent
Guttman

[11] Patent Number: 5,421,980
[45] Date of Patent: Jun. 6, 1995

[54] CAPILLARY ELECTROPHORESIS USING REPLACEABLE GELS

[75] Inventor: Andras Guttman, Palo Alto, Calif.

[73] Assignee: Beckman Instruments, Inc., Fullerton, Calif.

[21] Appl. No.: 272,714

[22] Filed: Jul. 8, 1994

Related U.S. Application Data

[60] Division of Ser. No. 793,256, Nov. 13, 1991, Pat. No. 5,332,481, which is a continuation of Ser. No. 647,071, Jan. 29, 1991, abandoned.

[51] Int. Cl.⁶ .................... G01N 27/26; G01N 27/447
[52] U.S. Cl. .............................. 204/299 R; 204/182.8
[58] Field of Search .......................... 204/299 R, 182.8

[56] References Cited

U.S. PATENT DOCUMENTS

| | | | |
|---|---|---|---|
| 4,152,242 | 5/1979 | Makokawkeyoon | 204/299 R |
| 4,695,354 | 9/1987 | Sugihara et al. | 204/180.1 |
| 4,747,919 | 5/1988 | Anderson | 204/182.8 |
| 4,865,706 | 9/1989 | Karger et al. | 204/182.8 |
| 4,908,112 | 3/1990 | Pace | 204/299 R |
| 5,089,111 | 2/1992 | Zhu et al. | 204/180.1 |
| 5,181,999 | 1/1993 | Wiktarowicz | 204/180.1 |

FOREIGN PATENT DOCUMENTS

| | | |
|---|---|---|
| 340653 | 11/1989 | European Pat. Off. . |
| 354984 | 2/1990 | European Pat. Off. . |
| 9105084 | 4/1991 | WIPO . |

Primary Examiner—John Niebling
Assistant Examiner—John S. Starsiak, Jr.
Attorney, Agent, or Firm—William H. May; P. R. Harder; Janis C. Henry

[57] ABSTRACT

The filling of an internally coated capillary with a gel in its polymerized state without damaging the gel. The coating prevents bonding of the gel to the inside of the capillary, The gel comprises up to 6% acrylamide and 0–5% crosslinker. The gel can be advantageously and conveniently used in automated electrophoresis systems for automatic replacement of spent gel.

26 Claims, 2 Drawing Sheets

CAPILLARY ELECTROPHORESIS USING REPLACEABLE GELS

This is a division of application Ser. No. 07/793,256, filed Nov. 13, 1991, now U.S. Pat. No. 5,332,481, which is a continuation of application Ser. No. 07/647,071, filed Jan. 29, 1991, now abandoned.

BACKGROUND OF THE INVENTION

1. Field of the Invention

The present invention relates to capillary gel electrophoresis, and more particularly to refilling capillaries using a polymerized gel.

2. Description of Related Art

Electrophoresis is one of the most widely used separation techniques in the biologically related sciences. Molecular species such as peptides, proteins, and oligonucleotides (analytes) are separated by causing them to migrate at different rates in a separation medium under the influence of an electric field. The separation medium can be a buffer solution, or a low to moderate concentration of an appropriate gelling agent such as agarose or polyacrylamide. When gel separation medium is used, separation of analytes is partly based on their molecular sizes as the analytes are sieved by the gel matrix. Smaller molecules move relatively more quickly than larger ones through a gel of a given pore size which depends in part on the concentration of the polymer in the gel.

U.S. Pat. Nos. 4,855,706 and 4,865,707 to Barry L. Karger and Aharons Cohen describe gel compositions suitable for capillary electrophoresis. A fused silica capillary having inner diameter in the order of 75 $\mu$m is first filled with a mixture of acrylamide monomer and other ingredients and polymerization is then allowed to go to completion in the capillary. The time taken to complete polymerization is a minimum of one hour. The polymerized gel has a limited storage life. Also, performance of the gel deteriorates after a period of use. This may be due to gradual accumulation of macromolecules in the gel matrix after repeated runs. The applied electric field may cause disintegration of the polymer material after repeated use. In the past, the gel-filled capillary columns have to be discarded after their useful life.

The gel columns have heretofore been used in laboratory set-ups involving many manual steps, e.g. placement of buffer containers with respect to the ends of the gel column, etc. Also spent gel column has to be manually replaced by a new gel column. To take advantage of automation in carrying out electrophoresis, due considerations should be given to eliminate as many of the manual steps in the design of an automated electrophoresis system.

SUMMARY OF THE INVENTION

The present invention is directed to filling an internally coated capillary using gel which is polymerized before filling the capillary. The internal coating on the capillary walls prevents bonding of the gel to the capillary walls. The gel is of a composition which allows it to fill the capillary in its polymerized state without damage to the gel and to be removed from the capillary after the gel has expended its useful life. The capillary can then be refilled with fresh gel. This can be handled automatically by an automated capillary electrophoresis system.

In the illustrated embodiment, the formulation of the gel comprises up to 6% of acrylamide monomer and buffer. In addition, optional amounts of crosslinker, catalyst, initiator, urea, and other additives may be added to adjust for the desired pore size, separation efficiency and life of the gel. The composition results in a gel of a consistency which can be forced into and out of the internally coated capillary without damaging the gel.

DETAILED DESCRIPTION OF THE INVENTION

The following description is of the best presently contemplated mode of carrying out the invention. This description is made for the purpose of illustrating the general principles of the invention and should not be taken in a limiting sense. The scope of the invention is best determined by reference to the appended claims.

Figure 1:
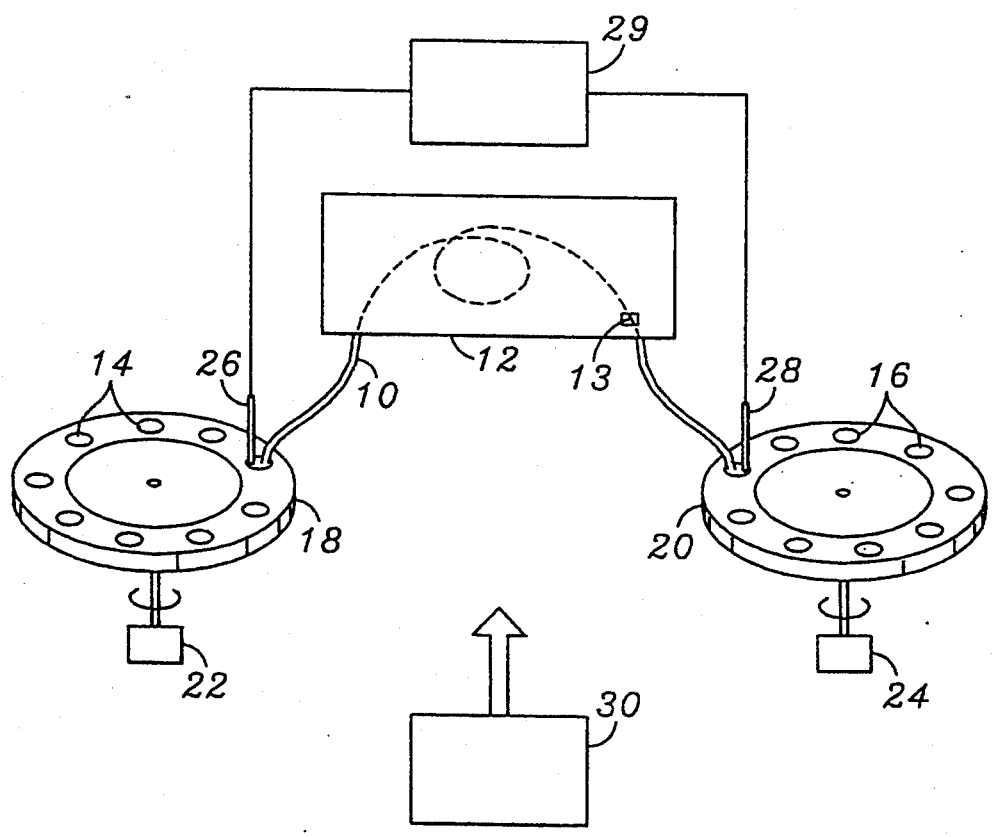
FIG. 1 is a schematic layout of an automated electrophoresis system.

The present invention can be used advantageously in conjunction with automated capillary electrophoresis systems, such as the P/ACE ™ 2000 electrophoresis system introduced by Beckman Instruments, Inc. Said system is schematically shown in FIG. 1. The details of the system have been described in copending U.S. patent applications Ser. No. 07/614,059; 07/542,673 and 07/187,760 commonly assigned to the assignee of the present invention and are incorporated by reference herein. In that system, the capillary column 10 is encased in a cartridge 12 which is supported to allow the ends of the capillary to access vials 14 and 16 of electrolyte or sample solutions. Capillary referred herein means tubing having inside diameter typically less than 1000 $\mu$m and more typically less than 300 $\mu$m. A detector 13 is provided to detect separated species. The vials are carried on carousels 18 and 20 which are rotated to position selected vials at the ends of the capillary. A selected solution can be forced into the capillary by submerging one end of the capillary into the vial and pressurizing the vial by means not shown (for details see copending applications). According to the present invention, the polymerized gel can be contained in a vial on the carousel and forced into an internally coated fused silica capillary in the same manner as is done with solution. The capillary walls are coated with a material (e.g. 50% phenyl and 50% methyl, or cynopropyl) to prevent bonding of the gel to the walls. Since the instrument has a built-in rinse mode which runs a rinsing solution (typically a buffer or electrolyte solution) through the capillary to clean the capillary, a rinsing solution can thus be used to wash out the spent gel. The capillary 10 can then be refilled with fresh gel. Alternative, instead of using a rinse solution, a supply of fresh gel can be used to displace the spent gel thus flushing and refilling the capillary in a single step. The above steps can be carried out automatically under control of microprocessor 30 programmed by the user. It can be seen that it would not be necessary to replace the entire gel capillary column 10 to replace the gel which would involve removing cartridge from the system and removing the column from the cartridge 12.

The P/ACE ™ system also has a sample injection mode which injects sample from a vial into one end of the capillary by either electromigration or pressure injection. Electrodes 26 and 28 are provided to apply the required high voltage (in the order of several hundred volts per cm of capillary) from voltage supply 29 for electromigration injection as well as for carrying out electrophoresis. Electrophoresis is performed with the two ends of the capillary dipped into electrolyte containing vials. The electrolyte can be in the form of buffer solution similar to the buffer the gel is made up of, or in the form of gel (i.e. a gel buffer system). In the latter case, the gel in the capillary can be replaced without having to position another vial.

The basic composition of the refillable gel is up to 6% acrylamide monomer dissolved in the appropriate buffer solution (usually 100 mM TRIS-borate of pH about 8.5). The acrylamide can be cross-linked with 0 to 5% of methylenebisacrylamide ("BIS"). 7M urea, hydrophilic polymer additives (e.g. polyethyleneglycol ("PEG")), an appropriate amount of catalyst (e.g. tetramethyleneethylenediamine ("TEMED") and initiator (e.g. ammonium persulfate) and other additives may be added to obtain a gel having the desired pore size, separation efficiency and life span. The steps for preparing the buffer and the gel are conventional and well known to one skilled in the art. Generally, the composition is allowed to polymerize overnight and the polymerized gel can be dialyzed or electrodialyzed against the gel buffer in order to remove the remaining ammonium persulfate, TEMED and the non-polymerized acrylamide and BIS-monomers if necessary. The coated inner surface of the fused silica capillary can be treated before the first filling of the gel. The surface can be treated by using 100% solution of methacryloxypropyltrimethoxysilane for 1 hour at 50° C. A diluted solution (diluted with methanol) may also be used. The silane is for "neutralizing" any hydroxide ions remaining on the capillary walls as a result of exposed silica due to slight imperfection in the coating. The presence of hydroxide ions is undesirable for some applications as it increases electroendoosmosis.

The capillary can be refilled with fresh gel of the same or different composition right after the previously spent gel has been removed from the capillary. Unlike the prior art gel columns where polymerization takes place in the capillary, it will not be necessary to wait for polymerization to take place in the present invention once the capillary has been filled with polymerized gel. This complements the automated features of the automated electrophoresis system and eliminates waiting time for changing of gel columns.

Up to 6% acrylamide without crosslinker, or up to 2% acrylamide +5% crosslinker, PEG of molecular weight up to 35,000 at concentration of up to 1% can be used is additive. Gels having high concentrations of polyacrylamide and crosslinker are too brittle to be able to be forced in their polymerized state to fill the capillary without damaging the gel. However, it is believed that gel having acrylamide greater than 6% may also maintain its integrity under special injection conditions. Since prior art gel-filled capillary columns do not have internal coating which prevents bonding of the gel to the capillary, the spent gel cannot be pushed out of the capillary effectively as the gel bonds to the capillary walls. It is noted that at concentration above 6% of acrylamide without crosslinker, an appropriate increase of PEG concentration and molecular weight is necessary to maintain the refillable property of the gel i.e. viscosity. Similarly, it has been found that in a composition having 5% BIS monomer and more than 2% acrylamide monomer, the PEG concentration and molecular weight should be increased.

Examples of specific compositions of the refillable gels according to the present invention which performance have been found to be comparable to prior art non-refillable gels are given below. The following examples are offered for illustrative purposes only, and are intended neither to define nor limit the invention in any manner.

EXAMPLE 1

100 mM TRIS
100 mM Boric Acid
3% T
0.5% C
2 mM EDTA (for separation of polynucleotides)
8.35 pH

EXAMPLE 2

100 mM TRIS
100 mM Boric Acid
1% T
5% C
2 mM EDTA (for separation of polynucleotides)
8.35 pH In both examples above, the acrylamide and crosslinker concentrations are expressed in %T and %C to characterize the gels. The definitions of %T and %C are as follows:

$$\% T = \frac{\text{mg acrylamide + mg crosslinker}}{\text{ml buffer volume}} \times 100$$

$$\% C = \frac{\text{mg crosslinker}}{\text{mg acrylamide + mg crosslinker}} \times 100$$

The total amount as well as the ratio of acrylamide and crosslinker determine the pore size and the pore distribution of a polyacrylamide gel. In the examples given, there is 2.985% acrylamide and 0.015% crosslinker (BIS) in Example 1 and 0.95% acrylamide and 0.05% crosslinker in Example 2. The crosslinker may be omitted in Example 1 if desired.

Figure 2:
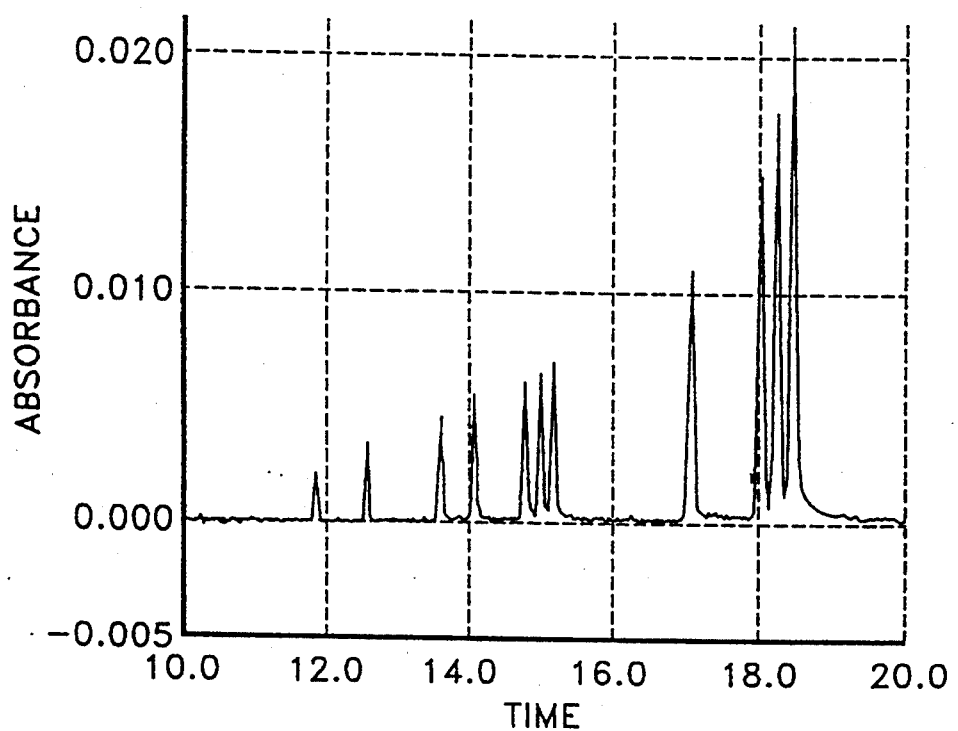
FIG. 2 is an electropherogram representing the results of electrophoresis using gel-injected into the capillary in polymerized state according to the present invention.

The results of electrophoresis using the gel of Example 1 is represented by the electropherogram in FIG. 2. The sample undergoing electrophoresis is φ-X 174 RF DNA-Hae III Digest mixture. The capillary column has an inner coating (e.g. OV-17) for preventing bonding of the gel to the capillary walls. The dimension of the capillary is 100 μm I.D., 47 cm total length with 40 cm effective length. The gel was polymerized and then injected into the capillary by using the rinse mode of the P/ACE ™ 2000 system. The sample is of 1 mg/ml concentration and is injected by electromigration into the gel column by applying 5 KV for 2 seconds. The electrophoresis is carried out under 12 KV and 33 μA.

Figure 3:
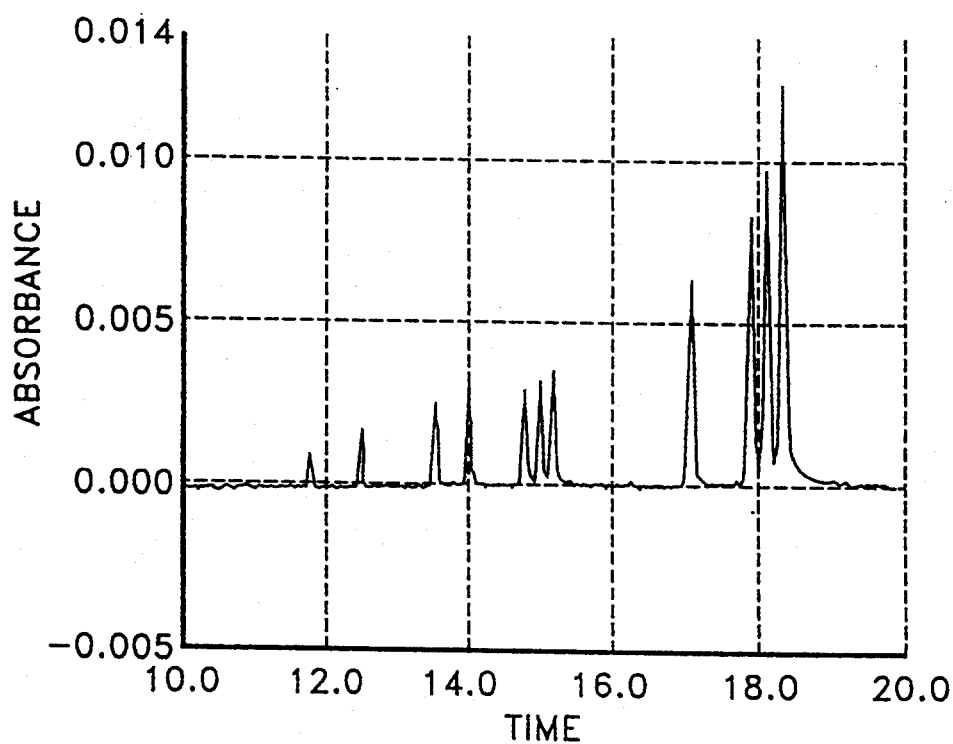
FIG. 3 is an electropherogram representing the results of electrophoresis using the same gel by which has been polymerized in the capillary.

The results in FIG. 2 can be compared to the results shown in FIG. 3 which represents the electropherogram of the same sample separated in a gel column having the same composition but which has the gel polymerized in the column. Sample injection and run parameters are the same. It is seen that the resolution of the peaks in the two electropherograms are quite similar. While the amplitudes between the two results differ somewhat, it is however not as much a concern as peak resolution for purposes of gel electrophoresis analysis as it is not a quantitative analysis.

Accordingly, it has been demonstrated that gel columns that have been refilled according to the present invention provide substantially the same separation efficiency, power and resolution as compared to the same gel polymerized in the capillary. The gel is not damaged as it is being forced into the coated capillary in its polymerized state thereby maintaining its separation performance. The refillable gel can be used advantageously in automated electrophoresis systems in which the task of replacing fresh gel can be handled automatically. A series of runs including changing of gel between runs can be programmed to be performed automatically without user intervention.

While the invention has been described with respect to the preferred embodiments in accordance therewith, it will be apparent to those skilled in the art that various modifications and improvements may be made without departing from the scope and spirit of the invention. Accordingly, it is to be understood that the invention is not to be limited by the specific described embodiments, but only by the scope of the appended claims.

I claim:

1. An apparatus for separating a sample into its molecular species comprising:
   a capillary;
   a supply of polymerized gel disposed in communication with one end of the capillary;
   means for filling the capillary with the polymerized gel;
   means for introducing the sample into the filled capillary; and
   means for performing electrophoresis on the sample to separate the sample into its molecular species.

2. A system as in claim 1 further comprising means for removing spent gel from the capillary so that it can be refilled with polymerized gel.

3. A system as in claim 2 further comprising means for automatic control of operation of the system.

4. A system as in claim 1 wherein the polymerized gel and sample are contained in receptacles and wherein the system further comprises a carousel for supporting the receptacles and means for turning the carousel to position the carousel to position the respective receptacle in flow communication with the capillary.

5. A system as in claim 4 wherein the means for filling the capillary and introducing the sample comprises means for pressurizing the receptacles in order to effect gel filling and sample introducing.

6. A system as in claim 5 further comprising means for automatic control of operation of the system.

7. A system as in claim 6 wherein the means for automatic control is programmed to displace spent gel originally in the capillary by filling polymerized gel from the receptacle into the capillary.

8. A system as in claim 7 further comprising means for analyzing electrophoretically separated components of the sample.

9. A system as in claim 8 further comprising a cartridge for supporting the capillary.

10. A system as in claim 1 wherein the capillary has inner walls coated with a material that prevents bonding of the polymerized gel to the walls.

11. A system as in claim 10 wherein the polymerized gel has a composition comprising up to 6% acrylamide and 0-5% crosslinker.

12. A gel-containing capillary column useful for electrophoresis comprising:
    a capillary having a bore coated with a material having a property which prevents bonding of gel to the material; and
    a polymeric gel filling said bore, wherein the gel has a composition that allows it to be forced to fill the bore substantially without damage to gel structure which might otherwise significantly affect the electrophoretic performance of the gel.

13. A capillary column as in claim 1 wherein the gel comprises:
    up to 6% of acrylamide; and
    0-5% of crosslinker.

14. A capillary column as in claim 13 wherein the crosslinker comprises methylenebisacrylamide.

15. A capillary column as in claim 14 wherein the coated material contains either phenyl groups and methyl groups or cyanopropyl groups.

16. A capillary electrophoresis system comprising:
    a capillary;
    a supply of polymerized gel disposed in communication with one end of the capillary;
    a supply of sample;
    means for filling the capillary with the gel and introducing a sample into the capillary; and
    means for performing electrophoresis.

17. A system as in claim 16 further comprising means for removing the gel from the capillary so that it can be refilled with gel.

18. A system as in claim 17 further comprising means for automatic control of the operation of the system.

19. A system as in claim 26 wherein the gel and sample are contained in receptacles and wherein the system further comprises a carousel for supporting the receptacles and means for turning the carousel to position the carousel to position the respective receptacle in flow communication with the capillary.

20. A system as in claim 19 wherein the means for for filling the capillary and introducing the sample comprises means for pressurizing the receptacles in order to effect gel filling and sample introducing.

21. A system as in claim 20 further comprising means for automatic control of the operation of the system.

22. A system as in claim 21 wherein the means for automatic control is programmed to displace gel originally in the capillary by filling gel from the receptacle into the capillary.

23. A system as in claim 22 further comprising means for analyzing electrophoretically separated components of the sample.

24. A system as in claim 23 further comprising a cartridge for supporting the capillary.

25. A system as-in claim 16 wherein the capillary has inner walls coated with a material that prevents bonding of the gel to the walls.

26. A system as in claim 25 wherein the gel has a composition comprising up to 6% acrylamide and 0-5% crosslinker.

* * * * *